United States Patent [19]

Nowak et al.

[11] 3,952,070

[45] Apr. 20, 1976

[54] PROCESS OF OLEFIN METATHESIS

[75] Inventors: Edward N. Nowak, Uniontown; Kenneth J. Frech, Tallmadge, both of Ohio

[73] Assignee: The Goodyear Tire & Rubber Company, Akron, Ohio

[22] Filed: Sept. 23, 1974

[21] Appl. No.: 508,479

[52] U.S. Cl. .................... 260/683 D; 252/411 R; 260/666 A; 260/677 R
[51] Int. Cl.² .......................................... C07C 3/62
[58] Field of Search ........ 260/683 D, 677 R, 666 A; 252/411

[56] References Cited
UNITED STATES PATENTS

| | | | |
|---|---|---|---|
| 3,365,513 | 1/1968 | Heckelsberg | 260/683 |
| 3,444,262 | 5/1969 | Heckelsberg | 260/683 |
| 3,579,602 | 5/1971 | Reusser | 260/683 |
| 3,660,507 | 5/1972 | Reusser | 260/683 |
| 3,725,496 | 4/1973 | Kobylinski et al. | 260/683 |

*Primary Examiner*—Delbert E. Gantz
*Assistant Examiner*—C. E. Spresser
*Attorney, Agent, or Firm*—F. W. Brunner; J. Y. Clowney

[57] ABSTRACT

There is disclosed an improved process of olefin metathesis which employs catalysts which are tungsten oxides or tungsten sulfides on suitable supports. The improvement is the pretreatment of such catalysts or the regeneration of such catalysts with ethylene or a butene at about 450°C to about 750°C.

10 Claims, No Drawings

PROCESS OF OLEFIN METATHESIS

This invention relates to an improved process for the disproportionation or metathesis of olefins. It relates in part to an improved process for the catalytic conversion of acyclic olefins, or mixtures thereof, into other acyclic olefins containing a higher and lower number of carbon atoms. It also relates to reactions of cycloolefins. It also relates to a method of increasing the catalytic activity of catalysts useful in the olefin metathesis processes. It also relates to catalysts of increased activity useful for the metathesis of olefins and cycloolefins.

An olefin metathesis or olefin disproportionation is a reaction in which a unique bond reorganization process takes place whereby materials possessing carbon-to-carbon double bonds undergo a redistribution of constituents as depicted in the following equation:

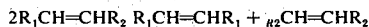

The olefin metathesis reaction being an equilibrium process facilitates the obtaining of olefins $R_1CH=CHR_1$ and $R_2CH=CHR_2$ starting from the olefin $R_1CH=CHR_2$ or alternatively obtaining $R_1CH=CHR_2$ from a mixture of olefins $R_1CH=CHR_1$ and $R_2CH=CHR_2$.

The olefin metathesis or olefin disproportionation reaction may be applied to a wide group of reactions. Representative of some of such reactions are as follows.

The disproportionation of an acyclic mono- or polyene having at least three carbon atoms into other acyclic mono- or polyenes of both higher and lower number of carbon atoms; for example, the disproportionation of propylene yields ethylene and butenes; the disproportionation of 1,5-hexadiene yields ethylene and 1,5,9-decatriene. The conversion of ethylene and an internal acyclic mono- or polyene having four or more carbon atoms to produce other olefins having a lower number of carbon atoms than that of the acyclic mono- or polyenes; for example, the conversion of ethylene and 4-methylpentene-2 yields 3-methylbutene-1 and propylene.

The conversion of an acyclic mono- or polyene having three or more carbon atoms and a different acyclic mono- or polyene having three or more carbon atoms to produce different acyclic olefins; for example, the conversion of propylene and isobutylene yields ethylene and isopentene.

The conversion of one or more cyclic mono- or cyclic polyenes to produce a cyclic polyene having a higher number of carbon atoms than any of the starting materials; for example, the conversion of cyclopentene yields 1,6-cyclodecadiene.

The conversion of an acyclic polyene having at least seven carbon atoms and having at least five carbon atoms between any two double bonds to produce acyclic and cyclic mono- and polyenes having a lower number of carbon atoms than that of the feed; for example, the conversion of 1,7-octadiene yields cyclohexene and ethylene.

The conversion of one or more acyclic polyenes having at least three carbon atoms between any two double bonds to produce acyclic and cyclic mono- and polyenes generally having both a higher and lower number of carbon atoms than that of the feed material; for example, the conversion of 1,4-pentadiene yields 1,4-cyclohexadiene and ethylene.

The conversion of ethylene or an acyclic mono- or polyene having three or more carbon atoms and a cyclic mono- or cyclic polyene to produce an acyclic polyene having a higher number of carbon atoms than that of any of the starting materials; for example, the conversion of cyclohexene and 2-butene yields 2,8-decadiene, the conversion of 1,5-cyclooctadiene and ethylene yields 1,5,9-decatriene.

The catalysts which are useful in this invention are those catalysts which will convert propylene into ethylene and butene or will convert 2-pentene into 2-butene and 3-hexene. These catalysts consist of the oxides and sulfides of tungsten. They may be defined as $WO_3$ and $WS_3$. These oxides and sulfides of tungsten are best supported on a conventional support, representative of which are silica, alumina, thoria, zirconia, titania, aluminum phosphate, zirconium phosphate, calcium phosphate, magnesium phosphate and titanium phosphate.

The catalysts of this invention are prepared by conventional techniques such as combining a catalyst grade silica, alumina, thoria, zirconia, titania, aluminum phosphate, zirconium phosphate, calcium phosphate, magnesium phosphate or titanium phosphate with a suitable tungsten compound such as ammonium tungstate or other soluble tungsten compounds. This material is then calcined by passing air or oxygen over these compounds at elevated temperatures, for instance, 500° to 750°C to convert the tungsten salt or compound to the tungsten oxide. Likewise, one or more of the group of aluminum phosphate, zirconium phosphate, calcium phosphate, magnesium phosphate, or titanium phosphate can be impregnated or even mixed with a suitable tungsten compound and calcined in a similar manner to convert the tungsten compounds to tungsten oxide. If the sulfide is desired, tungsten oxide impregnated on any of the supports is then treated with hydrogen sulfide at elevated temperatures such as 500°C to 750°C to convert the tungsten oxide to tungsten sulfide. Another method of preparation of either a tungsten sulfide or a tungsten oxide would be to grind and mix the tungsten oxide or tungsten sulfide with any of the support materials such as, for instance, zirconium or magnesium phosphate in a ball mill by heating at elevated temperatures in an inert atmosphere such as nitrogen. These mixtures could also be calcined in air at elevated temperatures to form the catalyst of this invention.

The catalyst of this invention which when prepared by these conventional methods should be activated before use. If these catalysts have been employed and have lost their activity due to the build up of coke or carbon and/or polymer on the catalyst surface they require regeneration. The activation or regeneration is accomplished using conventional techniques. Usually these techniques are straight forward, require no great discussion here. One may burn the carbon deposited or the coke deposited as well as any polymer from the catalyst by the simple expedient of passing a stream of dry air over the catalyst at elevated temperatures between about 500°C to about 750°C for a period of ½ hour or longer, usually followed by the treatment of the catalyst with a stream of dry nitrogen at from about 500°C to about 750°C for a period of approximately ½ hour or more. The gaseous hourly space velocity of these treatments may range from about 100 to about 10,000 volumes of dry air or nitrogen per volume of catalyst per hour.

It has been observed, however, that when such catalysts as those previously described in this application are employed to metathesize or disproportionate an acyclic olefin, such as propylene, the conversion of the propylene to other olefins containing higher or lower number of carbon atoms is extremely low at the beginning of any given run. It has been observed that a certain amount of time is required for the maximum conversion to be attained with a freshly prepared, activated catalyst such as that described previously. For instance, it has taken up to 200 minutes to reach maximum conversion of propylene which was passed over the catalyst at a temperature of 450°C at a GHSV of 190.

Therefore, it is an object of this invention to provide a method for increasing the immediate activity of an olefin metathesis catalyst. It is also an object to provide an improved catalyst for the olefin metathesis reaction. Other objects and advantages will become apparent from a study of the disclosure herein provided.

It has been discovered that an improvement in the conversion which may be obtained from an olefin metathesis catalyst which has undergone the conventional activation or regeneration if it subjected to pretreatment with a stream of ethylene or a butylene while at a temperature within the range of from about 450°C to about 750°C, preferably 500°C to 650°C, and a pressure from about 0 to about 500 psig, preferably from about 0 to about 100 psig. The time the catalyst is treated with the ethylene or a butylene may vary from about 0.1 minute to over 60 minutes or 15 to 30 minutes being preferred. These flow times if expressed in terms of volumes of gas per volume of catalyst per hour (GHSV) may vary from about 1 to about 5000 GHSV with from 100 to 2000 GHSV preferred. It has been found, however, the catalysts useful in the olefin metathesis reaction are subjected to a pretreatment with ethylene or a butylene prior to their use as an olefin metathesis catalyst that the maximum conversion can be obtained in the olefin metathesis reaction immediately without any further conditioning required by passing over this catalyst a stream of the olefin desired to be metathasized.

Olefins applicable for use in the metathesis process of the invention are acyclic mono- and polyenes having at least 3 carbon atoms per molecule including the cycloalkyl and aryl derivatives thereof; cyclic mono- and polyenes having at least 4 carbon atoms per molecule, including the alkyl and aryl derivatives thereof; mixtures of the above olefins; and mixtures of ethylene and the above olefins. Many useful reactions are accomplished with such acyclic olefins having 3–30 carbon atoms per molecule and with such cyclic olefins having 4–30 carbon atoms per molecule.

Some examples of acyclic olefins suitable for reactions of this invention include propylene, 1-butene, isobutene, 2-butene, 1,3-butadiene, 1-pentene, 2-pentene, isoprene, 1-hexene, 1,4-hexadiene, 2-heptene, 1-octene, 2,5-octadiene, 2,4,6-octatriene, 2-nonene, 1-dodecene, 2-tetradecene, 1-hexadecene, 5,6-dimethyl-2,4-octadiene, 2-methyl-1-butene, 2-methyl-2-butene, 1,3-dodecadiene, 1,3,6-dodecatriene, 3-methyl-1-butene, 1-phenylbutene-2,7,7-diethyl-1,3,5-decatriene, 1,3,5,7,9-octadecapentaene, 1,3-eicosadiene, 4-octene, 3-eicosene and 3-heptene, and the like, and mixtures thereof.

Some specific examples of cyclic olefins suitable for the reactions of this invention are cyclobutene, cyclopentene, cyclohexene, 3-methylcyclopentene, 4-ethyl-cyclohexene, 4-benzylcyclohexene, cyclooctene, 5-n-propylcyclooctene, cyclodecene, cyclododecene, 3,3,5,5-tetramethylcyclononene, 3,4,5,6,7-pentaethyl-cyclodecene, 1,5-cyclooctadiene, 1,5,9-cyclododecatriene, 1,4,7,10-cyclododecatetraene, 2-methyl-6-ethylcyclooctadiene-1,4, and the like, and mixtures thereof.

In the metathesis process wherein the catalysts of this invention are utilized, the olefins or mixtures of olefins are contacted with the pretreated olefin reaction catalyst at a temperature in the range of about 300°C to about 550°C at a pressure of about 0 to 2,000 psig and a reaction time in the range of about 0.1 second to 10 hours. With a fixed bed reactor and continuous operation, volume hourly space velocities in the range of 0.5 to 1,000 volumes of olefin per volume of catalyst per hour have produced excellent results. A more preferred range is 1 to 200 V/V/hour.

The invention is further illustrated by the following specific embodiments which should be considered as exemplary and should not be construed so as to limit unduly the invention.

EXAMPLE I

In order to illustrate that the metathesis of propylene over a catalyst composed of $WO_3$ on silica has an induction period, the following experiment was conducted.

There was placed in a ½ inch tubular stainless steel reactor contained within a cylindrical radiant heater, 10 cc of $(NH_4)_2W_4O_{13} \cdot 8 H_2O$ impregnated silica gel. This amount will yield 9 percent by weight of $WO_3$ based on the total weight of catalyst upon calcination. Nitrogen was passed through the catalyst bed at 1000 GHSV while the temperature was raised to 590°C. Next, dry air was passed through this catalyst bed at 1000 GHSV at 590°C for 1 hour. Nitrogen was then passed through the catalyst bed at 1000 GHSV for 1 hour. While maintaining the nitrogen flow, the reactor was cooled to 450°C. Propylene was brought on stream at 190 GHSV at 450°C. Samples of the reactor effluent were obtained and analyzed by gas chromatography. The results are given in Table 1.

TABLE I

| Sample | Time (Min) | % Butenes (wt %) | % Pentenes | *% Metathesis (wt %) |
|---|---|---|---|---|
| 1 | 5 | 4.0 | 0.3 | 6.1 |
| 2 | 23 | 8.6 | — | 12.8 |
| 3 | 38 | 14.9 | 0.5 | 22.3 |
| 4 | 76 | 20.5 | 1.4 | 30.7 |
| 5 | 104 | 22.7 | 1.9 | 34.0 |
| 6 | 178 | 24.7 | 2.6 | 37.0 |
| 7 | 221 | 25.0 | 2.9 | 32.5 |
| 8 | 238 | 24.5 | 2.9 | 36.8 |

*When appreciable amounts of ethylene were present, the gas chromatographic peak overlapped that of propylene, precluding quantitative determination. The percent metathesis was obtained by multiplying the weight percent of butenes by 1.5. (Since the weight of one mole of ethylene is 0.5 that of butene) This method was proved valid by comparison with mass spectral data.

The data in Table 1 indicates that considerable time is required to obtain maximum conversion or percent metathesis of the propylene.

EXAMPLE II

In order to illustrate that pretreatment of $WO_3$ on silica with ethylene will produce a catalyst having increased activity towards propylene methathesis, the following experiment was conducted.

In a ½ inch stainless steel tubular reactor was placed 10 cc of $(NH_4)_2W_4O_{13} \cdot 8H_2O$ impregnated silica gel. Nitrogen was passed through this catalyst bed at 1000 GHSV while the catalyst was heated to 590°C. Dry air was passed through the catalyst bed at 1000 GHSV at 590°C for one hour. Ethylene was passed through the catalyst bed at 1000 GHSV for 30 minutes at 590°C. The reactor was cooled to 450°C while maintaining the ethylene flow. Propylene was then passed into the catalyst at 190 GHSV at 450°C. Samples from the reactor effluent were obtained and analyzed by gas chromatography. The results are given in Table 2 below.

TABLE 2

| Sample | Time (min) | % Butenes | % Methathesis | % Pentenes |
|---|---|---|---|---|
| 1 | 10 | 24.3 | 36.4 | 3.3 |
| 2 | 26 | 24.8 | 37.2 | 3.4 |
| 3 | 41 | 24.3 | 36.5 | 3.0 |

The data in Table 2 demonstrate that the treatment of the calcinated catalyst with ethylene at 590°C substantially reduces the time required to obtain maximum catalytic activity in the metathesis of propylene.

EXAMPLE III

In this example, a catalyst was prepared as in Example II, except that the catalyst was treated by passing ethylene through the catalyst at 1000 GHSV for 30 minutes at 450°C. Propylene was brought on stream at 190 GHSV at 450°C. Samples were taken at various times and analyzed by gas chromatography. The results are given in Table 3.

TABLE 3

| Sample | Time (min) | % Butenes | % Pentenes | % Metathesis |
|---|---|---|---|---|
| 1 | 3.5 | 3.9 | — | 5.9 |
| 2 | 20 | 11.7 | — | 17.6 |
| 3 | 67 | 20.8 | 2.2 | 31.2 |
| 4 | 94 | 21.1 | 2.3 | 31.7 |
| 5 | 113 | 22.2 | 2.3 | 33.3 |
| 6 | 130 | 23.2 | 2.5 | 34.9 |
| 7 | 148 | 23.9 | 2.7 | 35.8 |
| 8 | 165 | 24.4 | 2.9 | 36.6 |

This data demonstrate that treatment with ethylene at 450°C is not quite as effective in reducing the time required to achieved maximum catalyst efficiency as is ethylene treatment at 590°C.

EXAMPLE IV

In order to illustrate that a pretreatment of $WO_3$ on silica with propylene at 590°C is not effective to prevent the induction period, the following experiment was conducted.

The catalyst was prepared as in Example III except that propylene was passed through the catalyst at 590°C for 30 minutes at 1000 GHSV instead of the ethylene. The reactor was cooled to 450° while maintaining the propylene flow and the propylene flow reduced to 190 GHSV. Samples of the reactor effluent were obtained as indicated in Example III. The results are given in Table 4.

TABLE 4

| Sample | Time (min) | % Butenes | % Pentene | % Metathesis |
|---|---|---|---|---|
| 1 | 6 | 3.0 | — | 4.5 |
| 2 | 20 | 2.1 | — | 3.2 |
| 3 | 74 | 2.4 | — | 3.6 |
| 4 | 120 | 6.9 | — | 10.4 |

This data demonstrate that pretreatment of the catalyst with propylene at 590° does not reduce the time required to achieve maximum catalytic effeciency as does ethylene.

EXAMPLE V

In order to illustrate that the pretreatment of the catalyst with ethylene without prior air activation is effective, the following experiment was conducted.

Ten cc of the catalyst of Example I, $(NH_4)_2 W_4O_{13} \cdot 8H_2O$ impregnated silica gel, was placed in the reactor. The reactor was heated to 590° under nitrogen flow at 1000 GHSV. Ethylene was then passed through the catalyst at 1000 GHSV at 590°C for 15 minutes. The reactor was cooled to 450° while still maintaining the ethylene flow. Propylene was then brought on stream at 190 GHSV at 450°C. Samples were obtained and results are given in Table 5 below.

TABLE 5

| Sample | Time | % Butenes | % Pentenes | % Metathesis |
|---|---|---|---|---|
| 1 | 2 | 11.2 | 0.9 | 16.8 |
| 2 | 4 | 21.2 | 3.1 | 31.8 |
| 3 | 9 | 19.6 | 2.9 | 29.3 |
| 4 | 25 | 21.9 | 3.5 | 32.9 |
| 5 | 45 | 21.8 | 3.5 | 32.7 |
| 6 | 63 | 21.9 | 3.9 | 32.9 |

The data in Table 5 demonstrate that the catalyst can be activated by relatively short treatment with ethylene instead of the conventional more time consuming air activation.

EXAMPLE VI

In order to illustrate that pretreatment of $WO_3$ on silica with a butene is effective to activate the catalyst, the following experiment was conducted.

An experiment was conducted similar to that of Example III except that the initial purge with nitrogen was for ten minutes only and that 2-butene was passed through the catalyst for 25 minutes at 1000 GHSV at 590°C and the reactor cooled to 450°C while the 2-butene flow maintained. Propylene was methathesized at 190 GHSV at 450°C. Samples of the effluent were obtained and the results are given in Table 6 below.

TABLE 6

| Sample | Time | % Butenes | % Metathesis | % Pentenes |
|---|---|---|---|---|
| 1 | 24 | 20.1 | 31.6 | 2.4 |
| 2 | 45 | 24.4 | 36.6 | 3.1 |

These data demonstrate that 2-butene is effective in pretreating the catalyst and is a means of substantially reducing the time required to achieve maximum catalytic activity in the metathesis of propylene.

Another unique advantage of the process of this invention is the regeneration of a so-called spent catalyst by treatment with ethylene without the use of an oxidizing gas as that previously described in this application.

For instance, utilizing a catalyst similar to those set forth in the previous examples, that is, tungsten oxide on silica, which had been on stream for some time and the metathesis activity decreased as indicated by analysis of the reactor effluent of a propylene metathesis to where the reactor effluent contained only 7.56 percent by weight of butene and which corresponded to 11.3 percent metathesis. At this time, the propylene flow was halted and nitrogen passed through the reactor and catalyst bed at 1000 GHSV while the reactor was heated to 590°C to remove all evidences of the hydrocarbon. While the reactor and the catalyst bed was maintained at 590°C, ethylene was introduced at 170 cc per minute for a period of 15 minutes. Following this treatment with ethylene, the reactor was cooled to 450° while maintaining the ethylene flow. The ethylene flow was halted and propylene was brought on stream at 32 cc per minute or 190 GHSV. A sample of the reactor effluent obtained 6 minutes later contained 24.8 percent by weight of butenes which corresponds to 37.3 percent metathesis. After 63 minutes, a second sample showed 24.9 percent by weight of butenes and 6.2 percent by weight of pentenes corresponding to 37.4 percent metathesis. This clearly demonstrates that a catalyst which has deteriorated in activity in the metathesis of propylene can be regenerated successfully with a treatment of the catalyst with ethylene without having to resort to an oxidizing gas such as air or oxygen.

Since in normal regeneration of such catalysts the oxidizing gas such as air or oxygen is normally required to remove the carbon deposits and/or the polymer deposits. Thus, it is illustrated that this time consuming step of utilizing an oxidizing or burning step can be eliminated by the practice of this invention.

A typical conventional regeneration procedure for supported metal oxides catalysts could be said to be improved for instance prior to the present discovery after the catalyst has been on stream for a given time, the catalytic activity decreases presumably due to coking or polymer laydown. At this time, in order to remove the deposits presumed responsible for the decreased activity, the feed stream (hydrocarbon) is interrupted. An inert gas ($N_2$, $A_7$, He, etc) is passed through the catalyst bed at the reaction temperature for a time sufficient to purge the feed hydrocarbon from the reactor. Continuing the inert gas flow, the temperature of the reactor is raised to 500°–750°C. Having attained the higher temperature, an oxidizing gas (air, $O_2$, etc) is passed through the reactor for a time sufficient to restore the catalytic activity to substantially its original level. This stage may proceed for several minutes to several hours. Having completed the regeneration at elevated temperature, the oxidizing gas is purged from the reactor with an inert gas ($N_2$, Ar, He, etc). Continuing the inert gas flow, the temperature of the reactor is lowered to the operating temperature. The hydrocarbon feed is again brought on stream.

A typical regeneration of a spent catalyst with ethylene would be, for instance, after the catalyst has been on stream for a given time, the catalytic activity decreases presumably due to coking or polymer laydown. At this time, in order to remove the deposits presumed responsible for the decreased activity, the feed stream (hydrocarbon) is interrupted. Ethylene is brought on stream (at less than 500 GHSV to more than 5000 GHSV) at the reactor temperature. Continuing the ethylene flow, the reactor is heated to 500°–750°C. This elevated temperature is maintained for 0.1 minute to 30 minutes or longer. Ten minutes to 30 minutes is preferred. Following this brief treatment, the reactor is cooled to the operating temperature while maintaining the ethylene flow. The hydrocarbon feed is again brought on stream.

Regeneration with ethylene offers the advantages that it is conducted much more simply with less equipment and fewer stages. Further, the off stream time is substantially reduced by using this regeneration procedure. Since catalysts are often regenerated 20, 100 or more times during use, reducing the regeneration time can result in substantial savings.

Thus, the invention is one where in a process of converting an olefin in an olefin metathesis reaction wherein at least one olefin selected from the group of cyclic and acyclic mono and polyene olefin hydrocarbons and mixtures of such hydrocarbons are converted in a reaction zone to products of the olefin metathesis reaction, which as defined herein, can be visualized as comprising the reaction between two first paris of carbon atoms, the two carbon atoms of each first pair being connected by an olefinic double bond, to form two new pairs from the carbon atoms of the said first pairs, the two carbon atoms of each said new pairs being connected by an olefinic double bond, in the presence of an olefin metathesis catalyst comprising an oxide of tungsten on a suitable support active for converting propylene into ethylene and butene, having an initial period of low activity under metathesis conditions including temperatures of from about 300°C to about 550°C and pressures of from about 0 to about 2000 psig and a reaction time in the range of from about 0.1 second to about 10 hours, the improvement comprising treating the catalyst with an olefin selected from the group comprising ethylene and butylenes at temperatures ranging from about 450°C to about 750°C for a period of time varying from about 0.1 minute to about 60 minutes prior to its use as an olefin metathesis catalyst.

The process of the invention can also be said to be a process where in an olefin metathesis process the catalyst for whatever reasons loses its activity, it can be regenerated by treating the $WO_3$ on a suitable support with ethylene or a butylene at temperatures from about 450°C to about 750°C for about 0.1 second to about 60 minutes.

While certain representative embodiments and details have been shown for the purpose of illustrating the invention, it will be apparent to those having skill in the art that certain modifications and changes may be made therein without departing from the spirit or scope of the invention.

What is claimed is:

1. In a process of converting an olefin in an olefin metathesis reaction wherein at least one olefin selected from the group of cyclic and acyclic mono and polyene olefin hydrocarbons and mixtures of such hydrocarbons are converted in a reaction zone to products of the olefin metathesis reaction, which as defined herein, can be visualized as comprising the reaction between two first pairs of carbon atoms, the two carbon atoms of each first pair being connected by an olefinic double bond, to form two new pairs from the carbon atoms of the said first pairs, the two carbon atoms of each said new pairs being connected by an olefinic double bond, in the presence of an olefin metathesis catalyst comprising an oxide of tungsten on a silica support active for converting propylene into ethylene and butene, having an initial period of low activity under metathesis conditions including temperatures of from about 300°C to about 550°C and pressures of from about 0 to about 2000 psig and a reaction time in the range of from about 0.1 second to about 10 hours, the improvement comprising treating the catalyst with an olefin selected from the group comprising ethylene and butylenes at temperatures ranging from about 450°C to about 750°C for a period of time varying from about 0.1 minute to about 60 minutes prior to its use as an olefin metathesis catalyst.

2. The process according to claim 1 wherein the olefin used to treat the catalyst is ethylene.

3. The process according to claim 1 wherein the olefin used to treat the catalyst is 2-butene.

4. The process according to claim 1 in which the olefin subjected to the olefin metathesis process is propylene.

5. The process according to claim 2 in which the olefin subjected to the olefin metathesis process is propylene.

6. In a process of converting an olefin in an olefin metathesis reaction wherein at least one olefin selected from the group of cyclic and acyclic mono and polyene olefin hydrocarbons and mixtures of such hydrocarbons are converted in a reaction zone to products of the olefin metathesis reaction, which as defined herein, can be visualized as comprising the reaction between two first pairs of carbon atoms, the two carbon atoms of each first pair being connected by an olefinic double bond, to form two new pairs from the carbon atoms of the said first pairs, the two carbon atoms of each said new pairs being connected by an olefinic double bond, in the presence of an olefin metathesis catalyst comprising an oxide of tungsten on a silica support active for converting propylene into ethylene and butene, under metathesis conditions including temperatures of from about 300°C to about 550°C and pressures of from about 0 to about 2000 psig and a reaction time in the range of from about 0.1 second to about 10 hours, said process having a decreased activity, the improvement comprising regenerating the catalyst by treating the catalyst with an olefin selected from the group comprising ethylene and butylenes at temperatures ranging from about 450°C to about 750°C for a period of time varying from about 0.1 minute to about 60 minutes prior to its use again as an olefin metathesis catalyst.

7. The process according to claim 6 in which the olefin used to regenerate the catalyst is ethylene.

8. The process according to claim 6 in which the olefin used to regenerate the catalyst is 2-butene.

9. The process according to claim 6 in which the olefin subjected to the olefin metathesis process is propylene.

10. The process according to claim 7 in which the olefin subjected to the olefin metathesis is propylene.

* * * * *